United States Patent [19]
Asanai et al.

[11] Patent Number: 5,993,982
[45] Date of Patent: Nov. 30, 1999

[54] METHOD AND APPARATUS FOR EVALUATING DURABILITY OF MAGNETIC DISK

[75] Inventors: Yoshimichi Asanai; Minoru Takahashi; Seigo Igaki; Masaki Kameyama, all of Kawasaki, Japan

[73] Assignee: Fujitsu Limited, Kawasaki, Japan

[21] Appl. No.: 08/965,638

[22] Filed: Nov. 6, 1997

[30] Foreign Application Priority Data

Mar. 18, 1997 [JP] Japan ........................... 9-065124

[51] Int. Cl.⁶ .................................................. B41M 3/12
[52] U.S. Cl. ...................................... 428/900; 427/127
[58] Field of Search .................................. 428/143, 323, 428/336, 694, 900, 128; 427/128; 364/556, 550, 551.01

[56] References Cited

U.S. PATENT DOCUMENTS 4,721,646  1/1988  Ikeda et al. ........................ 428/143
5,212,657  5/1993  Uchikawa et al. ................... 364/551

FOREIGN PATENT DOCUMENTS

| | | |
|---|---|---|
| 59-11578 | 1/1984 | Japan . |
| 63-187422 | 8/1988 | Japan . |
| 2-306136 | 12/1990 | Japan . |
| 3-53146 | 3/1991 | Japan . |
| 3-260902 | 11/1991 | Japan . |
| 4-155620 | 5/1992 | Japan . |
| 4-366746 | 12/1992 | Japan . |
| 5-142103 | 6/1993 | Japan . |
| 5-182386 | 7/1993 | Japan . |
| 5-264408 | 10/1993 | Japan . |

*Primary Examiner*—Merrick Dixon
*Attorney, Agent, or Firm*—Greer, Burns & Crain, Ltd.

[57] ABSTRACT

A method of evaluating a durability of a magnetic disk includes the steps of (a) obtaining conditions under which a sliding contact state of a first head with respect to a surface of a first magnetic disk stabilizes, and (b) causing a second head to make sliding contact with a surface of a second magnetic disk under the conditions and evaluating a durability of the second magnetic disk.

6 Claims, 11 Drawing Sheets

METHOD AND APPARATUS FOR EVALUATING DURABILITY OF MAGNETIC DISK

BACKGROUND OF THE INVENTION

The present invention generally relates to methods and apparatuses for evaluating the durability of magnetic disks, and more particularly to a method and an apparatus for evaluating the durability of a magnetic disk which is used in a magnetic disk unit.

In the magnetic disk unit which uses one or more magnetic disks, the so-called Contact Start Stop (CSS) system is employed. According to the CSS system, a head makes contact with a surface of the magnetic disk when the operation of the magnetic disk unit starts and when the operation of the magnetic disk unit ends. For this reason, a protection layer is provided on the surface of the magnetic disk, but still, frictional wear of the magnetic disk occurs due to the contact between the head and the magnetic disk.

On the other hand, due to the increase in the storage capacity and the recording density of the magnetic disk and also due to the decrease in the size of the magnetic disk unit, the floating distance of the head from the magnetic disk is becoming smaller. In addition, in order to prevent the head from being attracted to the surface of the magnetic disk and to ensure floating of the head from the magnetic disk, the surface of the magnetic disk is not perfectly flat and undulations are intentionally formed to a certain extent on the surface of the magnetic disk. As a result, the probability of the head making contact with the magnetic disk has increased.

For this reason, the durability of the magnetic disk has recently become an important factor which affects the performance of the magnetic disk unit. Hence, there are demands to realize a method and an apparatus which can efficiently and accurately evaluate the durability of the magnetic disk.

Conventionally, there is a method which evaluates the durability of the magnetic disk by rotating the magnetic disk at a low speed and preventing the head from floating from the magnetic disk.

In addition, a magnetic disk endurance testing method is proposed in Japanese Laid-Open Patent Application No.63-187422, for example. According to this first proposed method, the magnetic disk which is to be evaluated is rotated under vacuum of 100 mTorr or less, and the head is prevented from floating from the magnetic disk. Thus, the head makes sliding contact with respect to the surface of the magnetic disk, and the durability of the magnetic disk is evaluated by detecting the surface deterioration of the magnetic disk using an acoustic sensor.

Furthermore, a method of evaluating the head floating stability is proposed in Japanese Laid-Open Patent Application No.59-11578, for example. According to this second proposed method, the pressure is decreased in a range of 100 Torr to 1 Torr, and the time it takes for the head to make sliding contact with the surface of the magnetic disk after making contact with the magnetic disk is measured. This measured time is compared with a time which is similarly measured with respect to a standard head, so as to evaluate the head floating stability.

According to the conventional method of evaluating the durability of the magnetic disk described above, however, it takes an extremely long time to check the deterioration of the magnetic disk caused by the sliding contact between the head and the magnetic disk because the magnetic disk is rotated at the low speed. In addition, it is necessary to first clean the surface of the magnetic disk before the deterioration of the magnetic disk can be checked. For this reason, there was a problem in that the durability of the magnetic disk cannot be evaluated efficiently according to the conventional method.

On the other hand, according to the first proposed method described above, the magnetic disk which is to be evaluated is rotated under the vacuum of 100 mTorr or less and the head makes contact with the magnetic disk in this state. Further, the evaluation of the magnetic disk is made under the vacuum of 100 mTorr or less, regardless of the head: and the magnetic disk which are used. Consequently, there were problems in that an expensive apparatus is required to realize the vacuum state of 100 mTorr or less, it takes time to obtain the vacuum state, and the evaluation of the magnetic disk cannot be made within a short time.

Moreover, according to the second proposed method described above, the head makes contact with the magnetic disk which is rotated under the pressure of 100 Torr to 1 Torr. In addition, the evaluation of the magnetic disk is made under the pressure of 100 Torr to 1 Torr, regardless of the head and the magnetic disk which are used. As a result, there were problems in that an expensive apparatus is required to realize the pressure state of 100 Torr to 1 Torr, and although not as long as in the case of the first proposed method, it takes time to obtain the pressure state of 100 Torr to 1 Torr, and the evaluation of the magnetic disk cannot be made within a short time. Furthermore, the object of the second proposed method is to evaluate the head floating stability, and no mention is made of the evaluation of the durability of the magnetic disk.

SUMMARY OF THE INVENTION

Accordingly, it is a general object of the present invention to provide a novel and useful method and apparatus for evaluating the durability of a magnetic disk, in which the problems described above are eliminated.

Another and more specific object of the present invention is to provide a method and an apparatus for efficiently and accurately evaluating the durability of the magnetic disk.

Still another object of the present invention is to provide a method of evaluating the durability of a magnetic disk, comprising the steps of (a) obtaining conditions under which a sliding contact state of a first head with respect to a surface of a first magnetic disk stabilizes, and (b) causing a second head to make sliding contact with a surface of a second magnetic disk under the conditions and evaluating the durability of the second magnetic disk. According to the method of the present invention, it is possible to accurately evaluate the durability of the second magnetic disk within a short time because the second magnetic disk is evaluated under the conditions under which the sliding contact state of the first head with respect to the surface of the first magnetic disk stabilizes.

A further object of the present invention is to provide a durability evaluating apparatus for evaluating a durability of the magnetic disk, comprising first means for causing a second head to make sliding contact with a surface of a second magnetic disk under conditions which are obtained in advance and under which a sliding contact state of a first head with respect to a surface of a first magnetic disk stabilizes, and second means for evaluating the durability of the second magnetic disk. According to the durability evaluating apparatus of the present invention, it is possible to accurately evaluate the durability of the second magnetic disk within a short time because the second magnetic disk is evaluated under the conditions under which the sliding contact state of the first head with respect to the surface of the first magnetic disk stabilizes.

Other objects and further features of the present invention will be apparent from the following detailed description when read in conjunction with the accompanying drawings.

DESCRIPTION OF THE PREFERRED EMBODIMENTS

First, a description will be given of a first embodiment of a method of evaluating a durability of a magnetic disk according to the present invention.

Figure 1:
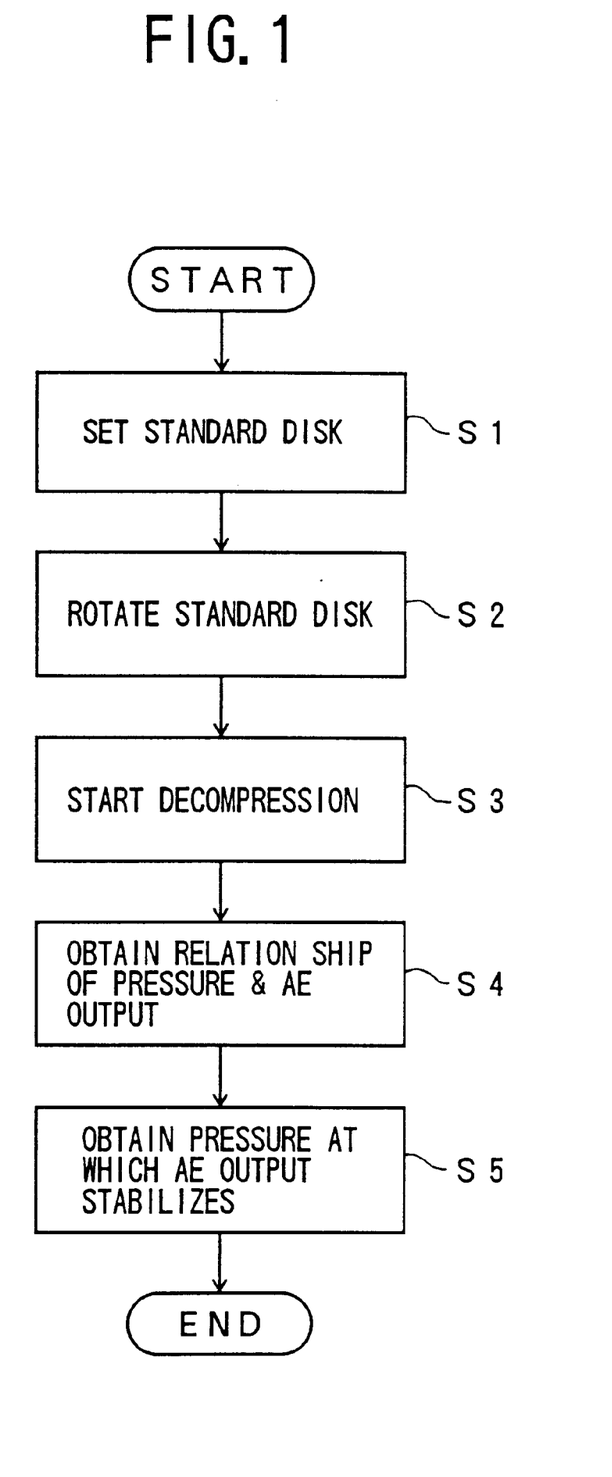
FIG. 1 is a flow chart for explaining a process of obtaining evaluating conditions in a first embodiment of a method of evaluating the durability of a magnetic disk according to the present invention.

FIG. 1 is a flow chart for explaining a process of obtaining evaluating conditions in this first embodiment of the method of evaluating the durability of the magnetic disk. In FIG. 1, a step S1 sets a standard magnetic disk in a durability evaluating apparatus (not shown). This standard magnetic disk is of the same kind or type as a magnetic disk which is to be evaluated. In addition, the durability evaluating apparatus is provided with a standard head which is of the same kind or type as a head which records signals on and reproduces signals from the magnetic disk which is to be evaluated. A step S2 rotates the standard magnetic disk which is set within the durability evaluating apparatus at 4776 rpm, for example, so that a peripheral speed. (relative velocity) is 15 m/sec at a radial position which is 30 mm from a center of the standard magnetic disk.

Figure 2:
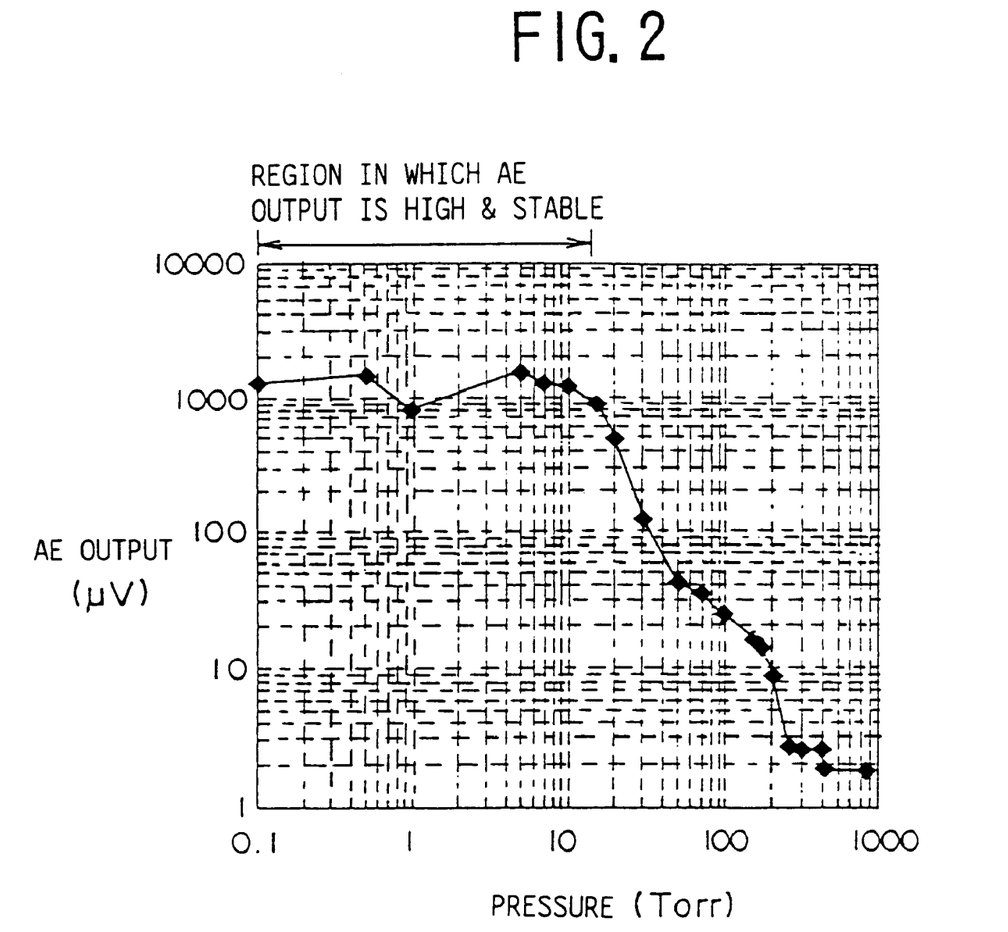
FIG. 2 is a diagram showing a relationship of a pressure within the durability evaluating apparatus and an output signal of an acoustic emission element.

A step S3 starts to decrease the pressure within the durability evaluating apparatus, and a step S4 detects an acoustic emission with respect to the surface of the standard magnetic disk by use of an acoustic sensor which is made up of an acoustic emission (AE) element. The step S4 also obtains a relationship between the pressure within the durability evaluating apparatus and an output signal of the AE element. FIG. 2 is a diagram showing the relationship which is obtained in the step S4. In FIG. 2, the ordinate indicates the output signal of the AE element in $\mu V$, and the abscissa indicates the pressure within the durability evaluation apparatus in Torr.

A step S5 obtains the pressure at which the output signal of the AE element stabilizes, that is, the conditions under which the sliding contact state of the standard head with respect to the surface of the standard magnetic disk stabilizes, based on the relationship shown in FIG. 2,. In order to decrease the pressure within the durability evaluating apparatus, the scale and cost of the durability evaluating apparatus become larger as the pressure becomes smaller due to the larger exhaust quantity, and moreover, the time it takes to obtain a desired low pressure becomes longer as the pressure becomes lower. For this reason, it is desirable that the pressure obtained in the step S5 is a maximum pressure at which the output signal of the AE element stabilizes in the relationship shown in FIG. 2. In this embodiment, the step S5 obtains the pressure of 15 Torr, for example, from the relationship shown in FIG. 2.

The durability of the magnetic disk also changes depending on the relative velocity between the head and the magnetic disk. Hence, it is desirable that the durability of the magnetic disk is evaluated at a relative velocity at which the durability of the magnetic disk does not change.

Figure 3:
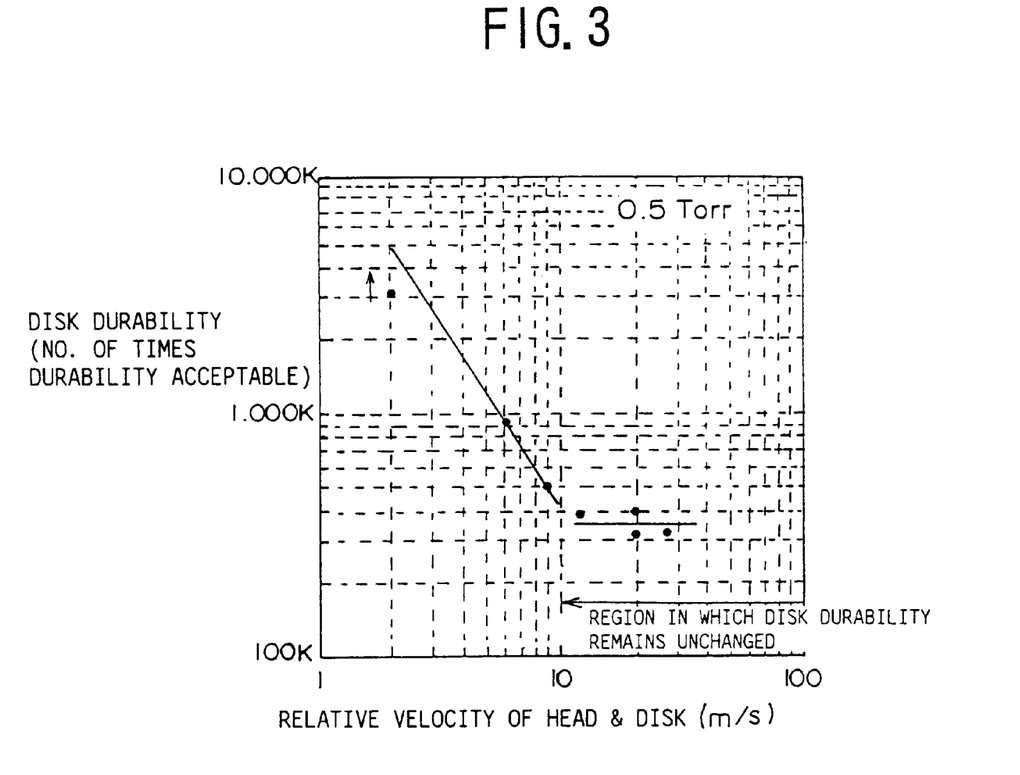
FIG. 3 is a diagram showing a relationship of a relative velocity between a standard head and a standard magnetic disk and the durability of the standard magnetic disk.

FIG. 3 is a diagram showing a relationship of the relative velocity between the standard head and the standard magnetic disk and the durability of the standard magnetic disk, which is obtained under the same conditions as in FIG. 2 at a pressure of 0.5 Torr. In FIG. 3, the ordinate indicates the number of times the evaluation result of the durability of the standard magnetic disk is acceptable, and the abscissa indicates the relative velocity between the standard head and the standard magnetic disk in m/sec. From FIG. 3, it may be seen that the durability of the standard magnetic disk does not change if the relative velocity is approximately 10 m/sec or greater. Accordingly, the step S5 shown in FIG. 1 may also obtain the relative velocity in addition to the pressure. In this case, the step S5 obtains the relative velocity at which the durability of the standard magnetic disk does not change, that is, the conditions under which the durability of the standard magnetic disk does not change, based on the relationship shown in FIG. 3. It is desirable that the relative velocity obtained in the step S5 is a maximum value at which the durability of the standard magnetic disk does not change in the relationship shown in FIG. 3 and to an extent such that an excessively large load is not applied on the durability evaluating apparatus, also from the point of view of reducing the evaluation time. In this embodiment, the step S5 obtains the relative velocity of 15 m/sec, for example, from the relationship shown in FIG. 3.

Of course, the step S5 may obtain at least one of the pressure at which the output signal of the AE element stabilizes and the relative velocity at which the durability of the standard magnetic disk does not change. In addition, if the relative velocity set in the step S2 is smaller than a minimum relative velocity obtained in the step S5, it is desirable to change the relative velocity set in the step S2 based on the relative velocity obtained in the step S5 and to carry out the steps S3 through S5 over again.

Figure 4:
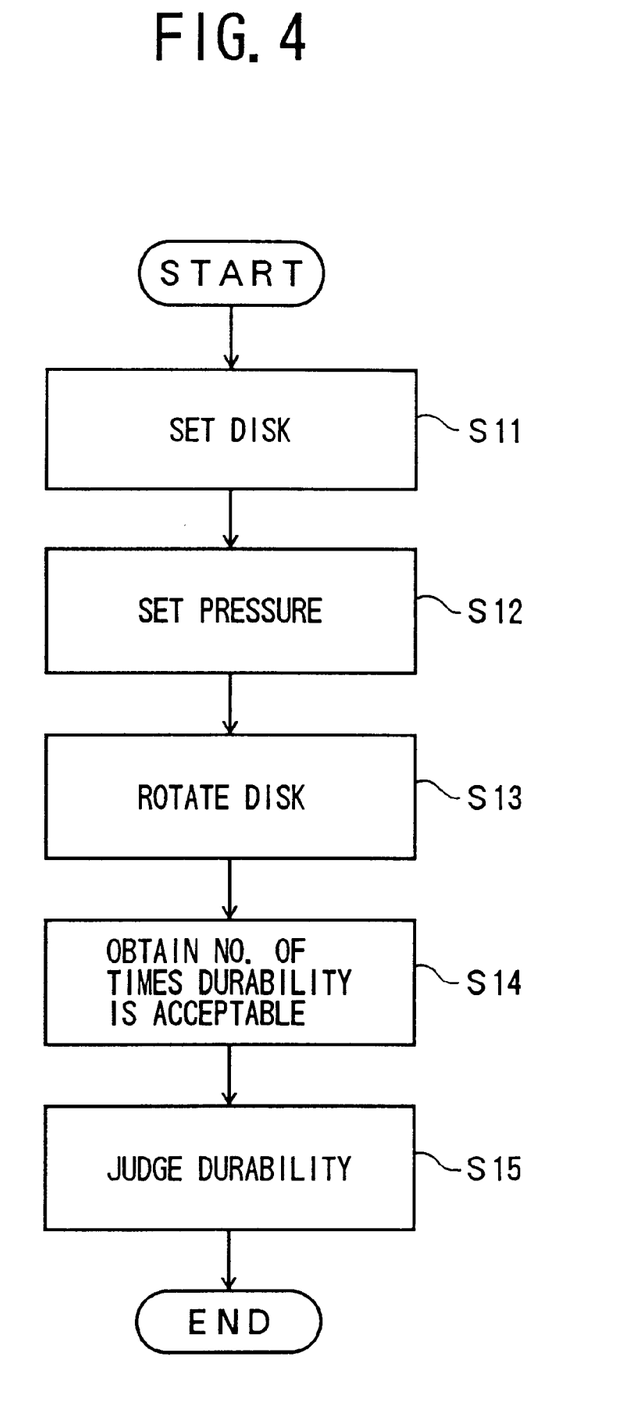
FIG. 4 is a flow chart for explaining an evaluation process in the first embodiment of the method of evaluating the durability of the magnetic disk.

FIG. 4 is a flow chart for explaining an evaluation process of this embodiment. In FIG. 4, in step S11 the magnetic disk which is to be evaluated is set in a durability evaluating apparatus (not shown) which is similar to the durability evaluating apparatus used in the process described above in conjunction with FIG. 1. A step S12 sets the pressure within the durability evaluating apparatus to the pressure obtained in the step S5 described above. The durability evaluating apparatus is provided with a head which is of the same kind or type as a head which records signals on and reproduces signals from the magnetic disk which is to be evaluated. This head within the durability evaluating apparatus makes contact with the surface of the magnetic disk by decreasing the pressure within the durability evaluating apparatus. A step S13 rotates the magnetic disk which is set within the durability evaluating apparatus under the same conditions as those of the step S2 described above. In other words, the magnetic disk is rotated at 4776 rpm so that the relative velocity becomes 15 m/sec at a radial position which is 30 mm from the center of the magnetic disk. As a result, the head within the durability evaluating apparatus makes sliding contact with the surface of the magnetic disk.

A step S14 evaluates the durability of the magnetic disk based on an output signal of an AE element, and obtains the number of times the evaluation result is acceptable. A step S15 decides whether or not the number of times the evaluation result is acceptable, obtained in the step S14, is greater than or equal to a reference value. It is judged that the durability satisfies a designed value if the number of times the evaluation result is acceptable is greater than or equal to the reference value. If an evaluation similar to that made in the step S14 is made in advance with respect to the standard magnetic disk, it is possible to determine the reference value based on the number of times the evaluation result of the standard magnetic disk is acceptable.

Figure 5:
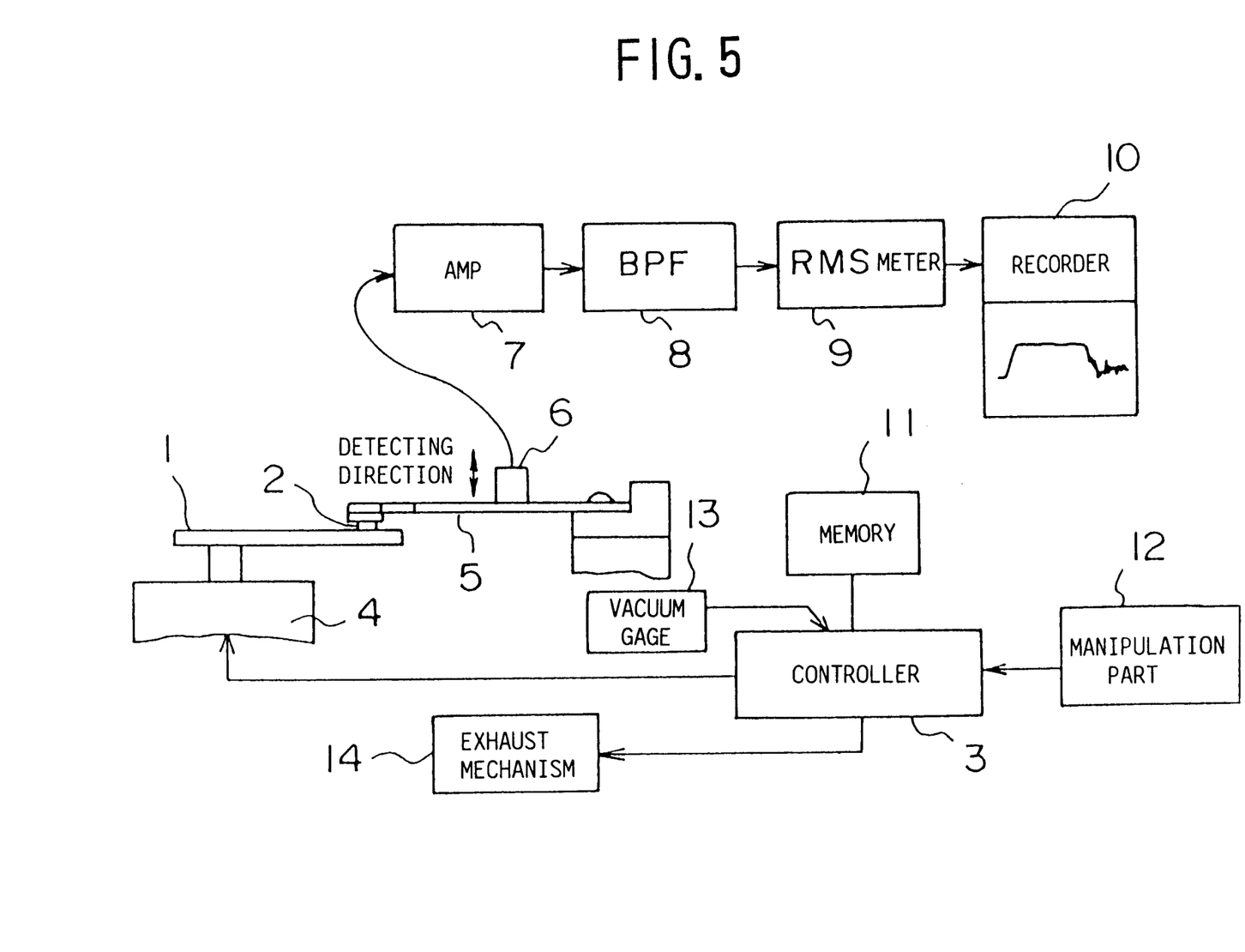
FIG. 5 is a diagram showing a first embodiment of a durability evaluating apparatus for evaluating a durability of a magnetic disk according to the present invention.

Next, a description will be given of a first embodiment of a durability evaluation apparatus for evaluating the durability of the magnetic disk according to the present invention. FIG. 5 is a diagram showing the first embodiment of the durability evaluating apparatus. This first embodiment of the durability evaluating apparatus employs the first embodiment of the method of evaluating the durability of the magnetic disk.

In FIG. 5, the durability evaluating apparatus generally includes a head 2, a controller 3, a driving part 4 having a spindle on which a magnetic disk 1 which is to be evaluated is set, an AE element 6 provided on an arm 5 which supports the head 2, an amplifier 7, a bandpass filter (BPF) 8, an effective value (RMS) meter 9, a recorder 10, a memory 11, a manipulate on part 12, a vacuum gage 13, and an exhaust mechanism 14.

The controller 3 controls the number of revolutions (or rotational speed) and the exhaust quantity of from exhaust mechanism 14, based on set values input form the manipulation part 12 or set values prestored in the memory 11. The set values include the value of the pressure within the durability evaluating apparatus and the value of the relative velocity between the head 2 and the magnetic disk 1, and are obtained in advance with respect to the standard magnetic disk which is of the same kind or type as the magnetic disk 1 according to the method described above in conjunction with FIG. 1. For example, the controller 3 is made of a central processing unit (CPU), and the memory 11 stores the set values described above, programs which are executed by the CPU, data and the like. In this embodiment, the controller 3 controls the exhaust mechanism 14 based on the set values described above while monitoring the pressure within the durability evaluating apparatus detected by the vacuum gage 13, so that the pressure within the durability evaluating apparatus is set to 15 Torr as described above. In addition, the controller 3 controls the driving part 4 based on the set values described above while carrying out a rotation control using a known feedback loop the illustration of which is omitted in FIG. 5 for the sake of convenience. Hence, the magnetic disk 1 is rotated at 4776 rpm so that the relative velocity at a radial position which is 30 mm from the center of the magnetic disk 1 is 15 m/sec. When the pressure within the durability evaluating apparatus is 15 Torr, the head 2 makes sliding contact with the surface of the magnetic disk 1 even while the magnetic disk 1 is rotated by the driving part 4.

The AE element 6 detects the AE with respect to the surface of the magnetic disk 1, and supplies an output signal voltage to the RMS meter 9 via the amplifier 7 and the BPF 8. Detecting directions of the AE element 6 are indicated by arrows in FIG. 5. The recorder 10 receives the measured result from the RMS meter 9, and the user can evaluate the durability of the magnetic disk 1 by monitoring an output of the recorder 10.

Out of the frequency components of the output signal voltage of the AE element 10, the frequency components which are to be monitored by the recorder 10 must be the frequency components which make a notable change in a vicinity of a break in the protection layer which is provided on the surface of the magnetic disk 1. These frequency components to be monitored are determined by the combination of the head 2 and the magnetic disk 1. Hence, the frequency components which make a notable change at the break in the protection layer of the standard magnetic disk are obtained in advance using the combination of the standard head and the standard magnetic disk which are of the same kind or type as the combination of the head 2 and the magnetic disk 1.

Figure 6:
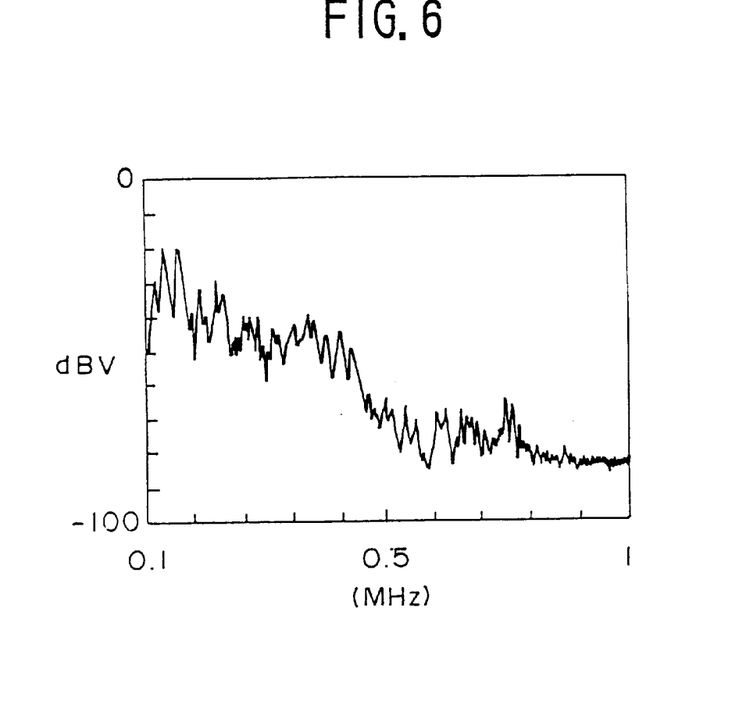
FIG. 6 is a diagram showing frequency components of an output signal voltage of an acoustic emission element of the durability evaluating apparatus before a protection layer of the standard magnetic disk breaks.
Figure 7:
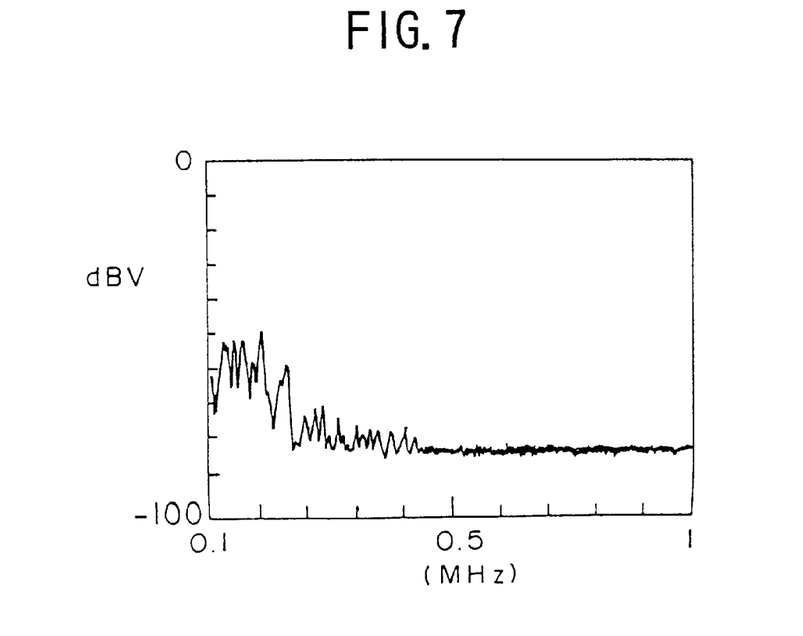
FIG. 7 is a diagram showing the frequency components of the output signal voltage of the acoustic emission element of the durability evaluating apparatus after the protection layer of the standard magnetic disk breaks.

FIG. 6 is a diagram showing the frequency components of the output signal voltage of the AE element of the durability evaluating apparatus before the protection layer of the standard magnetic disk breaks. In addition, FIG. 7 is a diagram showing the frequency components of the output signal voltage of the AE element of the durability evaluating apparatus after the protection layer of the standard magnetic disk breaks. In FIGS. 6 and 7, the ordinate indicates the amplitude of the output signal voltage of the AE element of the durability evaluating apparatus in dBV, and the abscissa indicates the frequency in MHz. It may be seen from FIGS. 6 and 7 that the frequency components of approximately 0.1 MHz make a notable change at the break in the protection layer of the standard magnetic disk in this case, and thus, the recorder 10 is set to output the frequency components of approximately 0.1 MHz.

Figure 8:
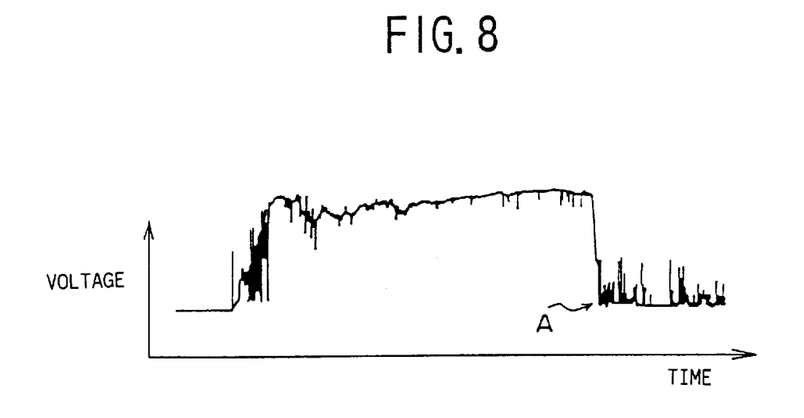
FIG. 8 is a diagram showing an output obtained from a recorder.

FIG. 8 is a diagram showing the output of the recorder 10 which is obtained in this case. In FIG. 8, the ordinate indicates the output signal voltage of the AE element 6 in arbitrary units, and the abscissa indicates the time in arbitrary units. In FIG. 8, the output signal voltage of the AE element 6 suddenly becomes small at a point A, and it is possible to accurately detect the break in the protection layer of the magnetic disk 1 from this sudden change at the point A. Accordingly, by comparing the time at which a sudden change such as that at the point A occurs and the time at which a sudden change occurs with respect to the standard magnetic disk by carrying out a similar process with respect to the standard magnetic disk, it is possible to evaluate the durability of the magnetic disk 1.

Figure 9:
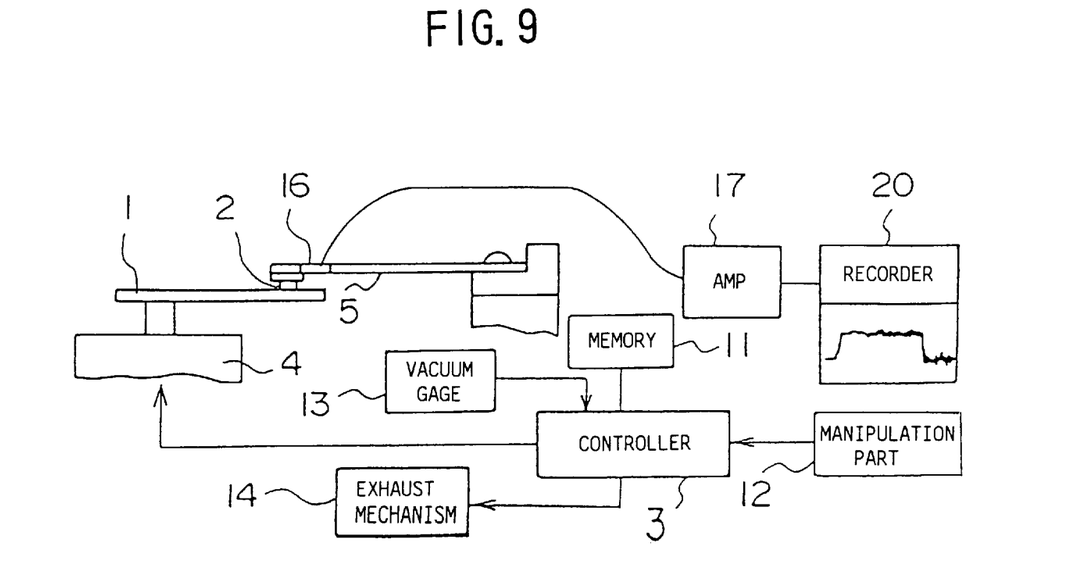
FIG. 9 is a diagram showing a second embodiment of the durability evaluating apparatus for evaluating the durability of the magnetic disk according to the present invention.

Next, a description will be given of a second embodiment of the durability evaluating apparatus for evaluating the magnetic disk according to the present invention. FIG. 9 is a diagram showing the second embodiment of the durability evaluating apparatus. In FIG. 9, those parts which are the same as those corresponding parts in FIG. 5 are designated by the same reference numerals, and a description thereof will be omitted. This second embodiment-of the durability evaluating apparatus employs a second embodiment of the method of evaluating the durability of the magnetic disk.

In FIG. 9, a strain gage 16 is provided on the arm 5. This strain gage 16 detects a frictional force along the in-plane direction of the magnetic disk 1 in a state where the head 2 makes contact with the magnetic disk 1. An output signal voltage of the strain gage 16 is supplied to a recorder 20 via an amplifier 17.

Figure 10:
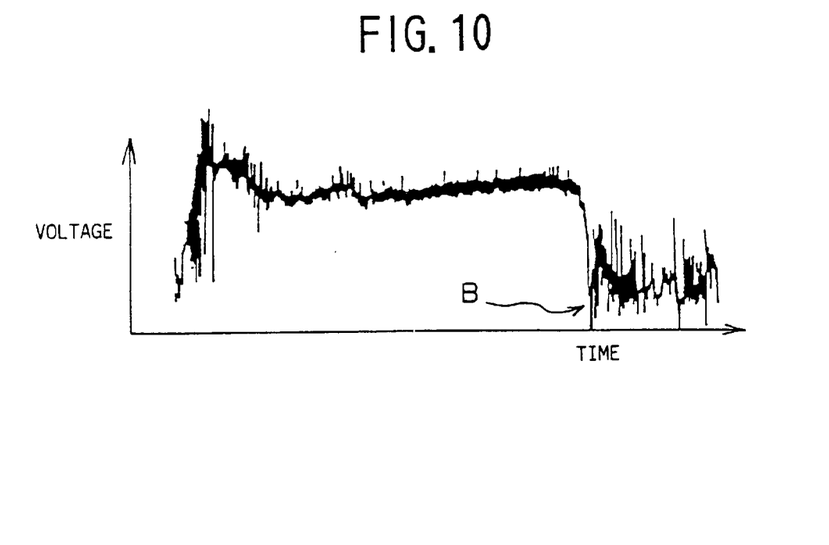
FIG. 10 is a diagram showing an output obtained from the recorder.

FIG. 10 is a diagram showing an output of the recorder 20 which is obtained in this case. In FIG. 10, the ordinate indicates the output signal voltage of the strain gage 16 in arbitrary units, and the abscissa indicates the time in arbitrary units. In FIG. 10, the output signal voltage of the strain gage 16 suddenly becomes small at a point B, and it is possible to accurately detect the break in the protection layer of the magnetic disk 1 from this sudden change at the point B. Accordingly, by comparing the time at which a sudden change such as that at the point B occurs and the time at which a, sudden change occurs with respect to the standard magnetic disk by carrying out a similar process with respect to the standard magnetic disk, it is possible to evaluate the durability of the magnetic disk 1.

Therefore, according to this second embodiment of the method of evaluating the durability of the magnetic disk, the output signal voltage of the strain gage 16 is used to detect the break in the protection layer of the magnetic disk 1 instead of using the output signal voltage of the AE element 6 used in the first embodiment of the method of evaluating the durability of the magnetic disk.

Figure 11:
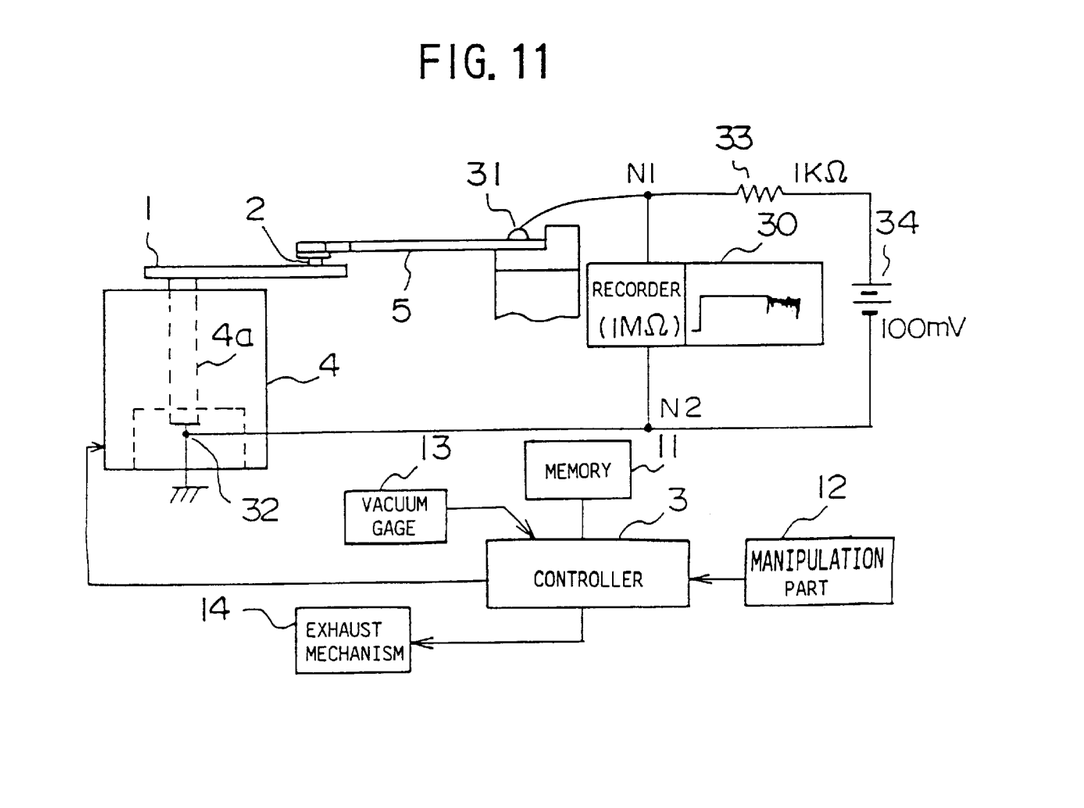
FIG. 11 is a diagram showing a third embodiment of the durability evaluating apparatus for evaluating the durability of the magnetic disk according to the present invention.

Next, a description will be given of a third embodiment of the durability evaluating apparatus for evaluating the magnetic disk according to the present invention. FIG. 11 is a diagram showing the third embodiment of the durability evaluating apparatus. In FIG. 11, those parts which are the same as those corresponding parts in FIG. 5 are designated by the same reference numerals, and a description thereof will be omitted. This third embodiment of the durability evaluating apparatus employs a third embodiment of the method of evaluating the durability of the magnetic disk.

In FIG. 11, an electrode 31 is provided on the arm 5. This electrode 31 is electrically connected to the head 2 and to a node N1. In addition, an electrode 32 is also provided. This electrode 32 is electrically connected to the magnetic disk 1 via a spindle 4a of the driving part 4, and to a node N2. A resistor 33 and a power supply 34 are connected in series to form a series circuit, and a recorder 30 is coupled in parallel to this series circuit. A parallel connection of the recorder 30 and the series circuit is coupled between the nodes N1 and N2. For example, the resistor 33 has a resistance of 1 kΩ, and a voltage of 100 mV is supplied by the power supply 34.

The protection layer of the magnetic disk 1 is made of an insulator, and the head 2 and the magnetic disk 1 become electrically connected at a break in the protection layer and the electrical resistance of the magnetic disk 1 changes if the protection layer breaks. Accordingly, when the head 2 makes sliding contact with the surface of the magnetic disk 1 and a voltage is applied across the nodes N1 and N2 from the power supply 34, the electrical resistance of the magnetic disk 1 suddenly changes if the break is generated in the protection layer, and a voltage which is proportional to the electrical resistance of the magnetic disk 1 and is monitored on the recorder 30 suddenly changes.

Figure 12:
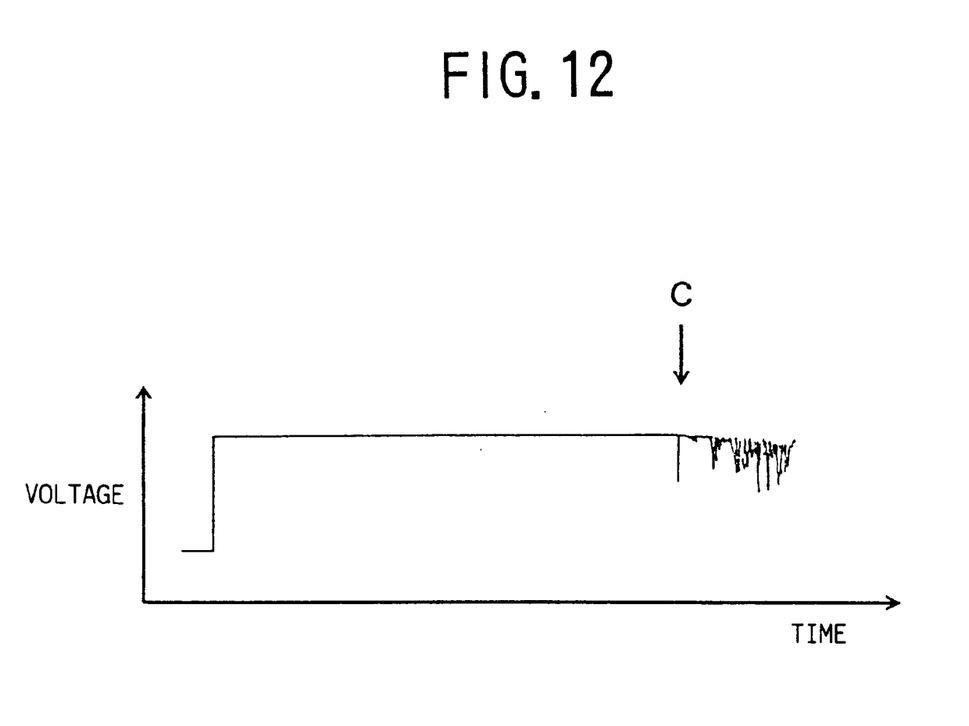
FIG. 12 is a diagram showing an output obtained from the recorder.

FIG. 12 is a diagram showing an output of the recorder 30 which is obtained in this case. In FIG. 12, the ordinate indicates the voltage across the nodes N1 and N2 in arbitrary units, and the abscissa indicates the time in arbitrary units. In FIG. 12, the voltage across the nodes N1 and N2, that is, the electrical resistance of the magnetic disk 1, suddenly becomes small at a point C, and it is possible to accurately detect the break in the protection layer of the magnetic disk 1 from this sudden change at the point C. Accordingly, by comparing the time at which a sudden change such as that at the point C occurs and the time at which a sudden change occurs with respect to the standard magnetic disk by carrying out a similar process with respect to the standard magnetic disk, it is possible to evaluate the durability of the magnetic disk 1.

Therefore, according to this third embodiment of the method of evaluating the durability of the magnetic disk, the electrical resistance of the magnetic disk 1 is used to detect the break in the protection layer of the magnetic disk 1 instead of using the output signal voltage of the AE element 6 used in the first embodiment of the method of evaluating the durability of the magnetic disk.

Of course, it is possible to combine two or more embodiments out of the first through third embodiments of the method and apparatus for evaluating the durability of the magnetic disk, in order to improve the reliability of the durability evaluation. When combining two or more embodiments, it is possible to judge that a break is generated in the protection layer of the magnetic disk 1 when the break is detected by at least one of the embodiments, and the durability of the magnetic disk 1 may be evaluated based on this judgement.

Figure 13A:
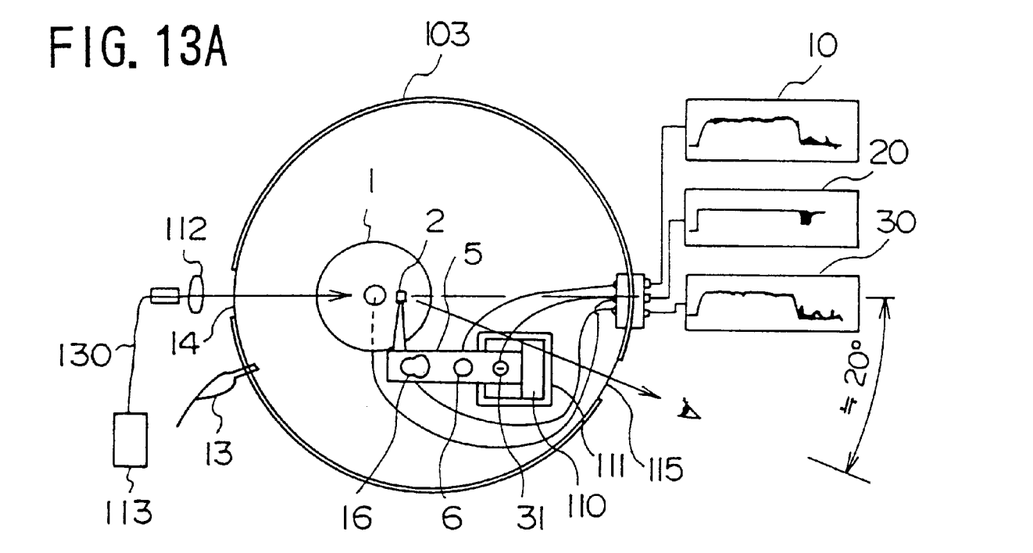
FIGS. 13A and 13B respectively are a plan view and a side view in cross section showing a fourth embodiment of the durability evaluating apparatus for evaluating the durability of the magnetic disk according to the present invention.
Figure 13B:
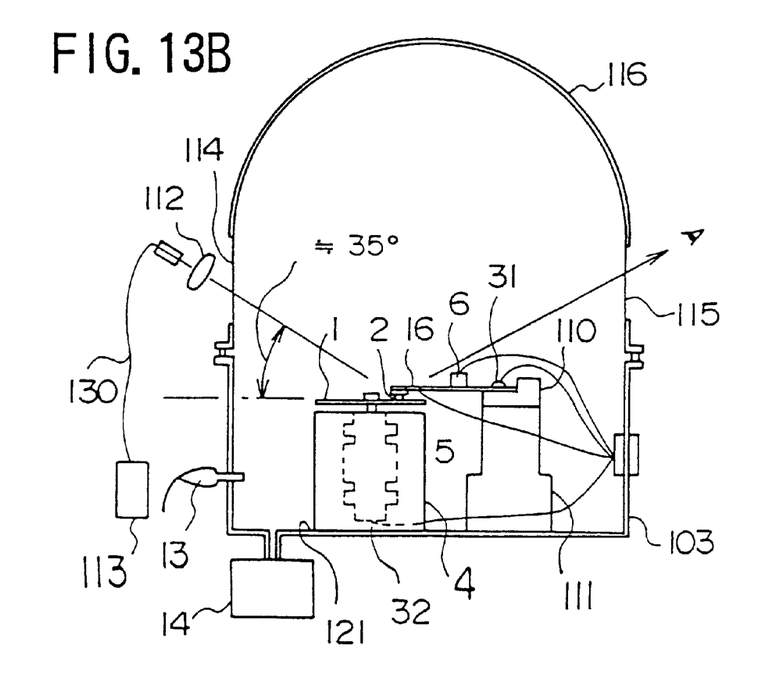

Next, a description will be given of a fourth embodiment of the durability evaluating apparatus for evaluating the magnetic disk according to the present invention. FIGS. 13A and 13B respectively are a plan view and a side view in cross section showing the fourth embodiment of the durability evaluating apparatus. In FIGS. 13A and 13B, the illustration of the control system is omitted, and those parts which are the same as those corresponding parts in FIGS. 5, 9 and 11 are designated by the same reference numerals, and a description thereof will be omitted. This fourth embodiment of the durability evaluating apparatus employs a fourth embodiment of the method of evaluating the durability of the magnetic disk. This fourth embodiment combines the first through third embodiments of the method and apparatus for evaluating the durability of the magnetic disk described above.

In FIGS. 13A and 13B, a head mounting part 111, the driving part 4 and the like are provided on a base 121 within a decompression chamber 103. The arm 5 is mounted on the head mounting part 111 via an insulation block 110. The exhaust mechanism 14 includes a vacuum pump. A light from a halogen lamp. 113 passes through an optical fiber 130, a convex lens 112 and a light irradiating window 114 provided in the decompression chamber 103, and is irradiated on the surface of the magnetic disk 1 as shown in FIG. 13B at an incident angle of approximately 35° with respect to the surface of the magnetic disk 1. A light blocking film 116 is provided on the outer peripheral surface or the inner peripheral surface of the decompression chamber 103 excluding the light irradiating window 114 and an observation window 115 which is used to observe a reflected light as will be described later. The surface portion of the magnetic disk 1 irradiated by the light can be observed through the observation window 115. As shown in FIG. 13A, this observation window 115 is provided at a position which is deviated by approximately 20° from a regular reflecting direction of the light irradiated on the magnetic disk 1, and thus, it is possible to accurately observe the surface of the magnetic disk 1.

Of course, the halogen lamp 113, the optical fiber 130, the convex lens 112 and the like may be provided within the decompression chamber 103.

Figure 14:
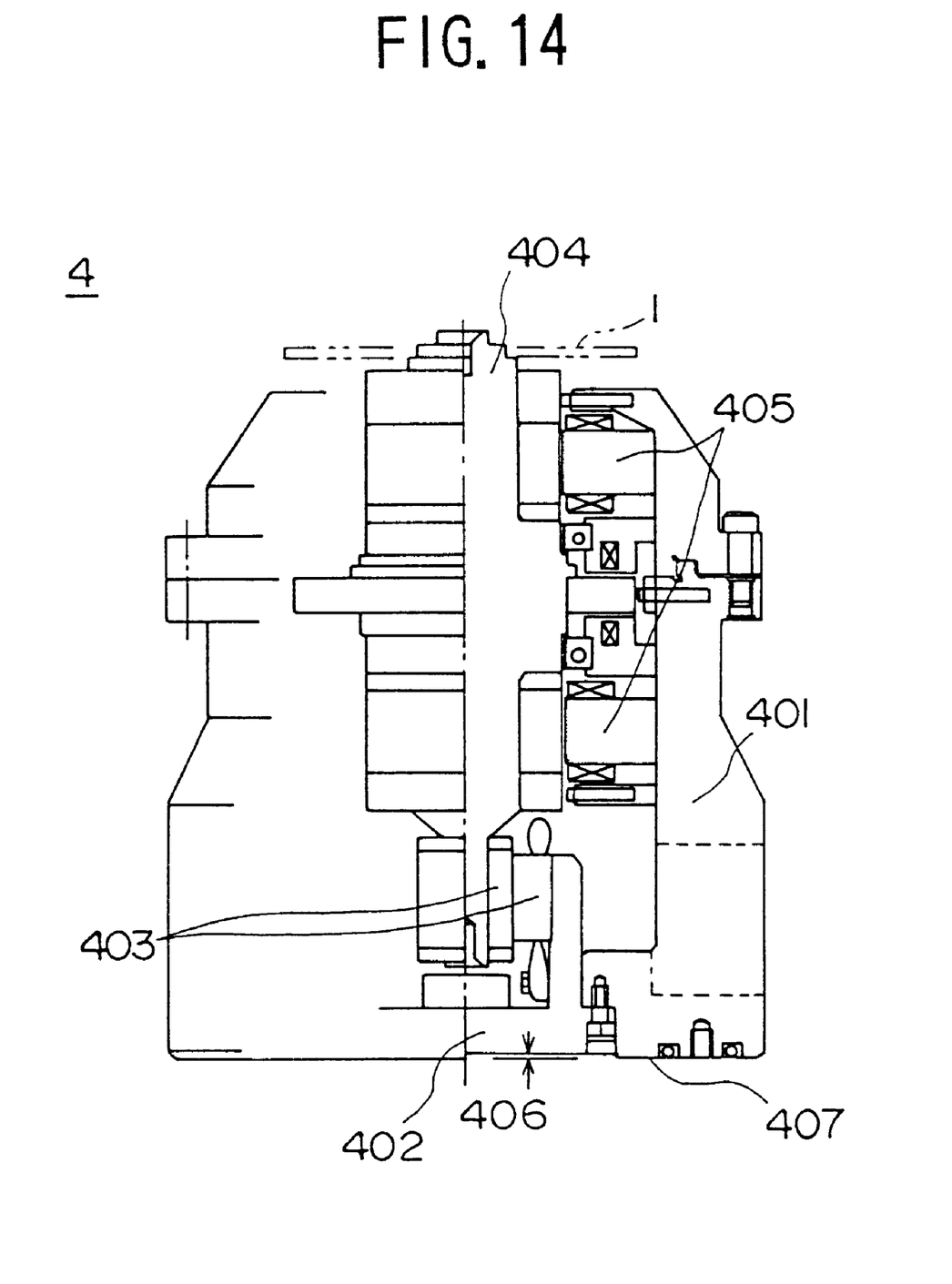
FIG. 14 is a side view in cross section showing a part of an embodiment of a driving part.

FIG. 14 is a side view in cross section showing a part of an embodiment of the driving part 4. In FIG. 14, the driving part 4 is provided with a magnetic bearing spindle of a type having a built-in motor. The driving part 4 generally includes a spindle housing 401, a motor coil housing 402, a built-in motor part 403, a spindle part 404, a magnetic bearing part 405, a stepped part 406, and a contact part 407. The spindle housing 401 and the motor coil housing 402 are respectively made of a material having a high thermal conduction such as aluminum, aluminum alloy, copper and copper alloy. The spindle housing 401 is mounted on the base 121 shown in FIG. 13B, and the contact part 407 which makes contact with the base 121 has a relatively large area. Vacuum grease fills the stepped part 406 between the, motor coil housing 402 and the spindle housing 401.

In a case where the diameter of the magnetic disk 1 is small, the magnetic disk 1 must be-rotated at a high rotational speed in order to obtain-a large relative velocity between the head 2 and the magnetic disk 1. However, in the case of a spindle using a mechanical bearing, the vibration becomes large at a rotational speed of approximately 10000 rpm, and the surface of the magnetic disk 1 undergoes a large vibration or wobble. Furthermore, in the case of the mechanical bearing, it is difficult to take measures against heat that is generated and to take measures with respect to the magnetic shielding of the rotary part which is necessary to maintain the decompression state. Accordingly, the spindle using the mechanical bearing is unsuited for evaluating the durability of the magnetic disk. On the other hand, in the case of a spindle using an air bearing, the vibration of the surface of the magnetic disk 1 is small even when the rotational speed of the magnetic disk 1 is high. But the spindle using the air bearing is also unsuited for evaluating the durability of the magnetic disk 1 because it is not possible to blow air at the bearing within the decompression chamber.

In the case of the driving part 4 shown in FIG. 14, it is possible to efficiently radiate the heat generated at the driving part 4, and the temperature rise of the magnetic disk 1 can be prevented when the spindle rotates. In addition, it is possible to rotate the magnetic disk 1 at a high rotational speed while maintaining the vibration of the surface of the magnetic disk 1 small. Furthermore, since the magnetic disk 1 can be rotated stably at a high speed, it is possible to set the relative velocity between the head 2 and the magnetic disk 1 to a high value and evaluate the durability of the magnetic disk 1 with a high reliability, even in the case of a magnetic disk 1 having a small diameter. It is also possible to greatly reduce the evaluation time that is required to evaluate the durability of the magnetic disk 1.

Further, the present invention is not limited to these embodiments, but various variations and modifications may be made without departing from the scope of the present invention.

What is claimed is:

1. A method of evaluating a durability of a magnetic disk, comprising the steps of:

(a) determining conditions under which a sliding contact state of a first head with respect to a surface of a first magnetic disk stabilizes, wherein said conditions include at least one of a pressure at which said sliding contact state stabilizes out of pressures within a chamber which accommodates the first head and the first magnetic disk, and a relative velocity at which a durability of the first magnetic disk remains unchanged out of relative velocities between the first head and the first magnetic disk, and (b) causing a second head to make sliding contact with a surface of a second magnetic disk under said conditions and evaluating a durability of the second magnetic disk.

2. The method of evaluating the durability of the magnetic disk as claimed in claim 1, wherein the first head and the second head are of the same kind or type, the first magnetic disk and the second magnetic disk are of the same kind or type, and said step (a) obtains said conditions in advance.

3. The method of evaluating the durability of the magnetic disk as claimed in claim 1, wherein said step (b) detects a break in a protection layer provided on the surface of the second magnetic disk based on a detection result of at least one of a detection of an acoustic emission with respect to the surface of the second magnetic disk, a detection of a frictional force between the second head and the second magnetic disk, and a detection of an electrical resistance between the second head and the second magnetic disk.

4. The method of evaluating the durability of the magnetic disk as claimed in claim 1, wherein said step (b) includes irradiating a light obliquely to the surface of the second magnetic disk and observing the surface of the second magnetic disk at a position deviated from a regular reflecting direction of the light.

5. The method of evaluating the durability of the magnetic disk as claimed in claim 1, wherein said step (b) rotates the second magnetic disk by a magnetic bearing spindle of a type having a built-in motor.

6. The method of evaluating the durability of the magnetic disk as claimed in claim 1, wherein said step (a) obtains said conditions at a pressure within the range of between approximately 0.1 Torr to approximately 15 Torr.

* * * * *